US010546664B2

United States Patent
Yonekura et al.

(10) Patent No.: US 10,546,664 B2
(45) Date of Patent: *Jan. 28, 2020

(54) STRETCHABLE CONDUCTOR COMPOSITION, PASTE FOR FORMING STRETCHABLE CONDUCTOR, GARMENT COMPRISING WIRING COMPRISING STRETCHABLE CONDUCTOR COMPOSITION, AND METHOD FOR PRODUCING SAME

(71) Applicant: TOYOBO CO., LTD., Osaka (JP)

(72) Inventors: Hiromichi Yonekura, Shiga (JP); Satoshi Imahashi, Shiga (JP); Michihiko Irie, Shiga (JP); Takashi Kondo, Shiga (JP); Maki Kinami, Shiga (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/068,176

(22) PCT Filed: Jan. 10, 2017

(86) PCT No.: PCT/JP2017/000499
§ 371 (c)(1),
(2) Date: Jul. 5, 2018

(87) PCT Pub. No.: WO2017/122639
PCT Pub. Date: Jul. 20, 2017

(65) Prior Publication Data
US 2019/0013111 A1    Jan. 10, 2019

(30) Foreign Application Priority Data

Jan. 13, 2016  (JP) ................................ 2016-004413
Jan. 13, 2016  (JP) ................................ 2016-004414

(51) Int. Cl.
H01B 1/22 (2006.01)
H01B 5/14 (2006.01)
(Continued)

(52) U.S. Cl.
CPC ............... H01B 1/22 (2013.01); A41D 1/005 (2013.01); A41D 19/0027 (2013.01); H01B 1/02 (2013.01); H01B 5/14 (2013.01)

(58) Field of Classification Search
CPC ......... H01B 1/22; H01B 5/14; D06M 15/693; C08K 2003/3045; H05K 1/038
See application file for complete search history.

(56) References Cited

U.S. PATENT DOCUMENTS 6,309,563 B1   10/2001  Iino et al.
10,119,045 B2 * 11/2018  Kondo .................... C08K 3/08
(Continued)

FOREIGN PATENT DOCUMENTS

CN     201524078     7/2010
CN     102483972     5/2012
(Continued)

OTHER PUBLICATIONS

Notification of Reasons for Rejection dated May 28, 2019 in Japanese Patent Application No. 2018-166995 with English translation.

(Continued)

Primary Examiner — Mark Kopec
(74) Attorney, Agent, or Firm — Wenderoth, Lind & Ponack, L.L.P.

(57) ABSTRACT

The purpose of the present invention is to provide a stretchable conductor that can be used to form a film having good repeated stretching durability, a garment-type election device that has a wire using the stretchable conductor, and a method for producing the same. Conductive particles, (Continued)

preferably silver particles, a predetermined quantity of a specific barium sulfate, and a flexible resin component are mixed together to obtain a stretchable conductor composition. A sheet made from the stretchable conductor composition thus obtained has a low initial conductivity, and a high conductivity retention rate when repeatedly stretched. By cutting the stretchable conductor composition into a predetermined shape and affixing the composition to fabric or the like that constitutes a garment, it is possible to achieve a garment-type device having electrical wiring with high stretchability.

15 Claims, 1 Drawing Sheet

(51) Int. Cl.
  *A41D 1/00*       (2018.01)
  *A41D 19/00*      (2006.01)
  *H01B 1/02*       (2006.01)

(56) References Cited

U.S. PATENT DOCUMENTS

| | | | | |
|---|---|---|---|---|
| 2003/0054165 | A1* | 3/2003 | Yamanaka | B29C 55/005 |
| | | | | 428/343 |
| 2005/0095406 | A1 | 5/2005 | Gunzel et al. | |
| 2005/0277826 | A1 | 12/2005 | Dunseath, Jr. | |
| 2007/0119539 | A1 | 5/2007 | Gunzel et al. | |
| 2008/0312523 | A1 | 12/2008 | Dunseath | |
| 2009/0054758 | A1 | 2/2009 | Dunseath | |
| 2009/0117362 | A1* | 5/2009 | Schosseler | B29C 55/143 |
| | | | | 428/220 |
| 2010/0234715 | A1 | 9/2010 | Shin et al. | |
| 2010/0255742 | A1 | 10/2010 | Yun et al. | |
| 2012/0119626 | A1 | 5/2012 | Takahashi et al. | |
| 2012/0152599 | A1 | 6/2012 | Kitagawa et al. | |
| 2013/0019383 | A1 | 1/2013 | Korkala et al. | |
| 2013/0056249 | A1 | 3/2013 | Taguchi et al. | |
| 2013/0225966 | A1 | 8/2013 | Maciá Barber et al. | |
| 2013/0338472 | A1 | 12/2013 | Maciá Barber et al. | |
| 2014/0124257 | A1 | 5/2014 | Yoshihara et al. | |
| 2014/0202744 | A1 | 7/2014 | Kobayashi et al. | |
| 2014/0291589 | A1 | 10/2014 | Hata et al. | |
| 2014/0318699 | A1 | 10/2014 | Longinotti-Buitoni et al. | |
| 2015/0204697 | A1 | 7/2015 | Taguchi et al. | |
| 2016/0130471 | A1* | 5/2016 | Burrows | H05K 1/09 |
| | | | | 174/251 |
| 2017/0002181 | A1* | 1/2017 | Lehmann | C09C 1/3684 |
| 2017/0188949 | A1 | 7/2017 | Macia Barber et al. | |
| 2017/0224244 | A1 | 8/2017 | Kuwabara et al. | |
| 2017/0296123 | A1 | 10/2017 | Macia Barber et al. | |
| 2018/0020936 | A1* | 1/2018 | Kwon | A61B 5/0408 |
| | | | | 600/388 |
| 2019/0077930 | A1* | 3/2019 | Irie | B32B 27/08 |

FOREIGN PATENT DOCUMENTS

| | | |
|---|---|---|
| EP | 0 892 027 | 1/1999 |
| JP | 6-263899 | 9/1994 |
| JP | 10-95962 | 4/1998 |
| JP | 2000433055 | 5/2000 |
| JP | 2001-126541 | 5/2001 |
| JP | 2004-288956 | 10/2004 |
| JP | 2004-288957 | 10/2004 |
| JP | 2007-509779 | 4/2007 |
| JP | 2007-173226 | 7/2007 |
| JP | 2007-263833 | 10/2007 |
| JP | 2008-501453 | 1/2008 |
| JP | 2008-198425 | 8/2008 |
| JP | 2010-189795 | 9/2010 |
| JP | 2011-15817 | 1/2011 |
| JP | 2012-33674 | 2/2012 |
| JP | 2012-54192 | 3/2012 |
| JP | 2012-138260 | 7/2012 |
| JP | 2012-183302 | 9/2012 |
| JP | 3178230 | 9/2012 |
| JP | 2012-231018 | 11/2012 |
| JP | 2012-248399 | 12/2012 |
| JP | 2013-135358 | 7/2013 |
| JP | 2013-184024 | 9/2013 |
| JP | 5448736 | 3/2014 |
| JP | 2014-510596 | 5/2014 |
| JP | 2014-137860 | 7/2014 |
| JP | 2014-151018 | 8/2014 |
| JP | 2014-200559 | 10/2014 |
| JP | 2014-228507 | 12/2014 |
| WO | 2011/145411 | 11/2011 |
| WO | 2012/108502 | 8/2012 |
| WO | 2013/031958 | 3/2013 |
| WO | 2013/146254 | 10/2013 |
| WO | 2014/153896 | 10/2014 |
| WO | 2014/178207 | 11/2014 |
| WO | 2016/114298 | 7/2016 |

OTHER PUBLICATIONS

Notification of Reasons for Rejection dated Jun. 4, 2019 in Japanese Patent Application No. 2018-011962 with English translation.
Paul et al., "An investigation into the durability of screen-printed conductive tracks on textiles", Measurement Science and Technology, 25:1-11 (2014).
Third Party Observation submitted Feb. 2, 2017 in International (PCT) Application No. PCT/JP2016/050819, with English Translation.
International Search Report dated Mar. 29, 2016 in International (PCT) Application No. PCT/JP2016/050936.
Third Party Observation submitted Feb. 14, 2017 in International (PCT) Application No. PCT/JP2016/050936, with English Translation.
Inoue et al., "Application of Printing Process to Fabrication of E-textiles", Journal of the Surface Finishing Society of Japan, 64(11):577-581 (2013), with Partial English Translation.
International Search Report dated Apr. 19, 2016 in International (PCT) Application No. PCT/JP2016/050819.
Submission of Information by Third Parties dispatched on Sep. 12, 2017 in Japanese Application No. 2016-569476, with English translation.
Submission of Information by Third Parties dispatched on Sep. 12, 2017 in Japanese Application No. 2016-569498, with English translation.
Office Action dated May 29, 2018 in Japanese Application No. 2016-569498, with English translation.
Extended European Search Report dated Jul. 19, 2018 in European Application No. 16737369.5.
Office Action dated Aug. 7, 2018 in Japanese Application No. 2016-569476, with English translation.
Office Action dated Nov. 27, 2018 in Japanese patent application No. 2018-011962, with English translation.
Decision of Rejection dated Dec. 4, 2018 in Japanese patent application No. 2016-569476, with English translation.
Tada Yasunori, "A Characteristic Evaluation of an Undershirt for Measurement of Bioelectricity Using Conductive Ink Wires", Journal of textile Engineering, Jul. 2013, vol. 59, No. 6, p. 141-148.
Japanese Office Action dated Feb. 12, 2019 in Japanese patent application No. 2018-039115, with English translation.
Office Action dated Feb. 26, 2019 in Japanese patent application No. 2018-039114, with English Translation.
European Office Action dated Apr. 18, 2019 in European patent application No. 16737369.5.
Office Action dated Mar. 5, 2019 in Japanese Patent Application No. 2018-039116, with English translation.
Office Action dated Mar. 5, 2019 in Japanese Patent Application No. 2018-039119, with English translation.
Office Action dated Mar. 12, 2019 in Japanese Patent Application No. 2018-039117, with English translation.

(56) References Cited

OTHER PUBLICATIONS

International Search Report dated Apr. 18, 2017 in International (PCT) Application No. PCT/JP2017/000499.
Ahn et al., "Stretchable electronics: materials, architectures and integrations", Journal of Physics D: Applied Physics, vol. 45, 2012, 103001, pp. 1-14.
Chun et al., "Highly conductive, printable and stretchable composite films of carbon nanotubes and silver", Nature Nanotechnology, vol. 5, Dec. 2010, pp. 853-857.
Office Action dated Jul. 17, 2019 in U.S. Appl. No. 15/543,295.
Notification of Reasons for Rejection dated Aug. 27, 2019 in Japanese Patent Application No. 2018-466996 with English translation.
Office Action dated Nov. 4, 2019 in corresponding Chinese Patent Application No. 201680008764.7 with English translation.
Communication pursuant to Article 94(3 dated Nov. 5, 2019 in corresponding European Patent Application No. 16737369.5.
Notification of Reasons for Refusal dated Nov. 26, 2019 in corresponding Japanese Application No. 2018-039114, with English translation.
Notification of Reasons for Refusal dated Nov. 26, 2019 in corresponding Japanese Application No. 2018-166995, with English translation.
Extended European Search Report dated Nov. 21, 2019 in corresponding European Application No. 17738393.2.
Notice of Reasons for Refusal dated Dec. 3, 2019 in corresponding Japanese Application No. 2018-039116, with English translation.
Notice of Reasons for Refusal dated Dec. 3, 2019 in corresponding Japanese Application No. 2018-039119, with English translation.

\* cited by examiner

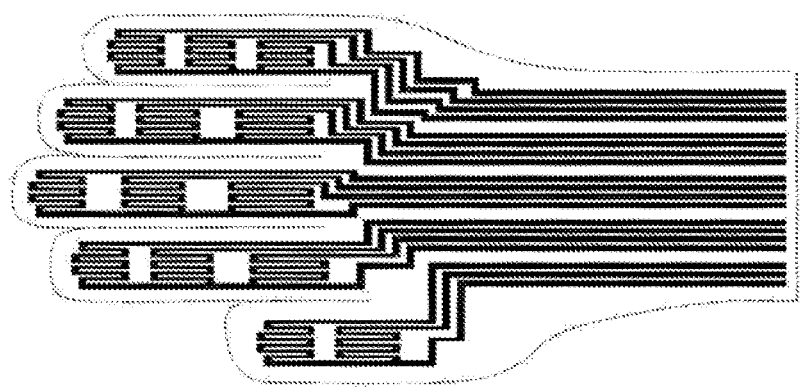

STRETCHABLE CONDUCTOR COMPOSITION, PASTE FOR FORMING STRETCHABLE CONDUCTOR, GARMENT COMPRISING WIRING COMPRISING STRETCHABLE CONDUCTOR COMPOSITION, AND METHOD FOR PRODUCING SAME

TECHNICAL FIELD

The present invention relates to a stretchable conductor used for an electrical wiring or the like. In particular, the present invention relates to a stretchable conductor which has improved durability against repeated elongation and which can be used for a wiring portion, an electrode portion, or the like when incorporating electronics into a garment or the like, a garment using the same, and a method for producing the garment.

BACKGROUND ART

Recently, a wearable electronic device intended to use an electronic device having input/output function, calculation function, and communication function in a state of being very close to or in close contact with a body has been developed. As such a wearable electronic device, devices with an accessory-type shape such as a wristwatch, eyeglasses, and earphones, and a textile-integrated device where electronic functions are incorporated into a garment are known.

An electrical wiring for power supply and signal transmission is necessary for an electronic device. In particular, for a textile-integrated wearable electronic device, the electrical wiring is required to have stretchability in accordance with a stretchable garment. Usually, an electrical wiring composed of a metal wire or metal foil inherently has no practical stretchability, and hence a technique for providing stretching capabilities in a pseudo manner by arranging a metal wire or metal foil in a wave shape or in a repeated horseshoes shape is employed.

In the case of the metal wire, it is possible to form a wiring by regarding the metal wire as an embroidery yarn and sewing it into a garment. However, it is clear that such a method is not suitable for mass production.

A method of forming a wiring by etching the metal foil is common as a method for producing a printed wiring board. A method is known in which the metal foil is attached to a stretchable resin sheet, and a wave-shaped wire is formed in the same manner as in the printed wiring board to make a stretchable wiring in a pseudo manner (Non-Patent Document 1). In this method, a stretchability is given in a pseudo manner by twist deformation of the wave-shaped wiring portion. However, metal foil varies also in the thickness direction due to the twist deformation, and thus if the metal foil is used as a part of a garment, the garment has uncomfortable wearing feeling, which is not preferable. In addition, when the metal foil undergoes excessive deformation due to washing or the like, permanent plastic deformation occurs in the metal foil, and the wiring may have the problem of the durability.

As a method to realize a stretchable conductor wiring, a method using a special conductive paste has been proposed. In such a method, conductive particles such as silver particles, carbon particles, and carbon nanotubes, elastomer such as urethane resin with stretchability, natural rubber, or synthetic rubber, and a solvent etc. are kneaded to form a paste, and using the resulting paste, a wiring is printed and drawn on a garment directly or in combination with a stretchable film substrate or the like.

A conductive composition composed of conductive particles and a stretchable binder resin can macroscopically realize a stretchable conductor. From a microscopic viewpoint, in the conductive composition obtained from the above-mentioned paste, the resin binder portion is deformed upon receiving an external force, and the conductivity is maintained within a range in which the electrical chain of the conductive particles is not broken. The resistivity observed macroscopically is higher than that of metal wires or metal foil. However, since the composition itself has stretchability, the wiring is not required to have a shape like a wave-shaped wiring, and flexibility in the width and the thickness of the wiring increases. Therefore, on a practical level, it is possible to realize a wiring with a low resistance compared with a metal wire.

Patent Document 1 discloses a technique in which silver particles and silicone rubber are combined, and the conductive film on the silicone rubber substrate is further covered with silicone rubber to suppress degradation of conductivity during elongation. Patent Document 2 discloses a combination of silver particles and a polyurethane emulsion and that a conductive film with high conductivity and a high elongation ratio can be obtained. Furthermore, many examples have also been proposed in which improvement of characteristics is attempted by combining conductive particles having a high aspect ratio such as carbon nanotubes, silver fillers, and the like.

RELATED ART DOCUMENTS

Patent Documents

Patent Document 1: JP-A-2007-173226
Patent Document 2: JP-A-2012-54192

Non-Patent Documents

Non-Patent Document 1: Jong-Hyun Ahn and Jung Ho Je, "Stretchable electronics:materials,architectures and integrations" J. Phys. D: Appl. Phys. 45(2012)103001
Non-Patent Document 2: Kyoung-Yong Chun,Youngseok Oh, Jonghyun Rho, Jong-Hyun Ahn, Young-Jin Kim, Hyoung Ryeol Choi and Seunghyun Baik, "Highly conductive, printable and stretchable composite films of carbon nanotubes and silver" Nature Nanotechnology, 5,853(2010)

DISCLOSURE OF THE INVENTION

Problems to be Solved by the Invention

However, in the above-mentioned composition in which conductive particles are blended with a resin, there is no particular bonding force between the conductive particles, and when the deformation is repeated, the electrical chain between the conductive particles may gradually break, thereby resulting in degradation of conductivity.

Means for Solving the Problems

As a result of careful consideration for solving the above problems, the inventors are found that the following means can solve the above problems and reached this invention.

The stretchable conductor composition of the present invention, which can accomplish the object described above, comprising at least conductive particles (a), barium sulfate particles (b), and a flexible resin (c) having a tensile elastic modulus of 1 MPa or more and 1000 MPa or less, wherein the barium sulfate particles (b) are contained in an amount of 2 to 30% by mass relative to the total amount of the conductive particles (a) and the barium sulfate particles (b), and the flexible resin (c) is contained in an amount of 7 to 35% by mass relative to the total amount of the conductive particles (a), the barium sulfate particles (b) and the flexible resin (c).

In a preferred embodiment of the present invention, the average particle diameter of the conductive particles as measured by a dynamic light scattering method is larger than the average particle diameter of the barium sulfate particles as measured by a dynamic light scattering method.

In a preferred embodiment of the present invention, the barium sulfate particles are subjected to a surface treatment with a hydroxide and/or oxide of one or both of Al and Si.

In a preferred embodiment of the present invention, the conductive particles comprise silver particles having an average particle diameter, as measured by a dynamic light scattering method, of 0.5 to 20 μm.

The present invention further includes a garment (an item of clothing) comprising an electrical wiring comprising the stretchable conductor composition as described above.

In a preferred embodiment of the present invention, the electrical wiring comprises a layer formed of a stretchable conductor containing carbon as a conductive filler on a surface of the electrical wiring.

In a preferred embodiment of the present invention, the electrical wiring comprises an insulating coating layer on a surface of the electrical wiring.

In a preferred embodiment of the present invention, the electrical wiring comprises an insulating layer on a surface of the electrical wiring, the surface being in contact with a fabric constituting the garment.

The present invention further includes a method for producing a garment (an item of clothing) comprising an electrical wiring, the method comprising: laminating a sheet formed of the stretchable conductor composition as described above on a fabric.

Effects of the Invention

The stretchable conductor composition of the present invention is a formed by blending metal particles, which are conductive particles, preferably silver particles, and barium sulfate particles, which are an insulator, into a flexible resin. Surprisingly, when barium sulfate particles are blended, degradation of conductivity due to repeated elongation is suppressed and a stretchable conductor with high durability can be obtained despite the fact that barium sulfate particles are an insulator. In addition, although the amount of the conductor component decreases as a whole, an influence on degradation of conductivity is extremely small. Barium sulfate particles have high dispersibility in a flexible resin that is a binder, and are expected to function as the core of resin deformation when the resin portion is deformed by an external force. The resin elongated by the external force shrinks when the external force is removed, but it does not return completely to its original state due to hysteresis. For this reason, the electrical chain between the conductive particles is broken and repeat durability is lowered. However, if the core is present, the resin tends to shrink locally as centered around the core when the external force is removed and the resin shrinks, so that compared with the case where the core is not present, the resin may be easily restored nearly to the state before elongation.

BRIEF DESCRIPTION OF THE DRAWINGS

The drawing is a wiring pattern diagram printed on a glove-type apparatus exemplified in the application example of the present invention.

MODE FOR CARRYING OUT THE INVENTION

The stretchable conductor composition according to one embodiment of the invention is described below.

The conductive particles (a) in the present invention are composed of a material having a specific resistance of $1 \times 10^{-1}$ Ωcm or less, and have a particle diameter of 100 μm or less. Examples of the material having a specific resistance of $1 \times 10^{-1}$ Ωcm or less include metal, alloy, carbon, doped semiconductor, conductive polymer, and the like. As the conductive particles preferably used in the present invention, metals such as silver, gold, platinum, palladium, copper, nickel, aluminum, zinc, lead, and tin, alloy particles such as brass, bronze, cupronickel, and solder, hybrid particles such as silver-coated copper, metal-plated polymer particles, metal-plated glass particles, metal-coated ceramic particles, and the like can be used.

In the present invention, it is preferred to mainly use flaky silver particles or an irregular-shaped aggregated silver powder. Here, the "mainly use" means that the amount of 90% by mass or more of the conductive particles is used. The irregular-shaped aggregated powder is made by three-dimensional aggregation of spherical or irregular-shaped primary particles. The irregular-shaped aggregated powder and the flaky powder are preferable because they have a specific surface area larger than that of spherical powder or the like, and hence an electrical conductivity network can be formed even when the filling amount is small. The irregular-shaped aggregated powder, which is not in a monodisperse form, is further preferable because the particles physically contact with each other, and hence an electrical conductivity network can be easily formed.

Although there is no particular limitation for the particle diameter of the flaky powder, the average particle diameter (50% D) measured by a dynamic light scattering method is preferably 0.5 to 20 μm, and more preferably 3 to 12 μm. If the average particle diameter exceeds 15 μm, the formation of a fine wiring may become difficult, and clogging occurs in the case of screen printing or the like. If the average particle diameter is less than 0.5 μm, the particles cannot contact with each other when the filling amount is small, and as a result, the electrical conductivity may deteriorate.

Although there is no particular limitation for the particle diameter of the irregular-shaped aggregated powder, the average particle diameter (50% D) measured by a light scattering method is preferably 1 to 20 μm, and more preferably 3 to 12 μm. If the average particle diameter exceeds 20 μm, the dispersibility decrease, and as a result, paste formation may become difficult. If the average particle diameter is less than 1 μm, the effects as the aggregated powder is lost, and as a result, high electrical conductivity may not be maintained when the filling amount is small.

As the barium sulfate particles (b) in the present invention, ground barite obtainable by grinding a barite mineral called a natural barite, and a so-called precipitated barium sulfate produced by a chemical reaction can be used. It is preferred in the present invention to use the precipitated barium sulfate of which particle diameter is easily controlled. The average particle diameter of the barium sulfate particles preferably used, as determined by a dynamic light scattering method, is preferably 0.01 to 18 µm, more preferably 0.05 to 8 µm, and further preferably 0.2 to 3 µm. In addition, the barium sulfate particles in the present invention are preferably subjected to a surface treatment with a hydroxide and/or oxide of one or both of Al and Si. By such a surface treatment, the hydroxide and/or oxide of one or both of Al and Si adhere to the surface of the barium sulfate particles. The adhering amount of these compounds is preferably 0.5 to 50, and more preferably 2 to 30 relative to 100 of barium elements at an element ratio detected by X-ray fluorescence analysis.

The average particle diameter of the barium sulfate particles is preferably smaller than the average particle diameter of the conductive particles. The number average particle diameter of the conductive particles is preferably 1.5 times or more, further preferably 2.4 times or more, and still further preferably 4.5 times or more of the number average particle diameter of the barium sulfate particles. When the average particle diameter of the barium sulfate particles exceeds the above range, the irregularities on the surface of the resulting coat increase, which tends to cause a fracture of the coat when stretched. On the other hand, when the average particle diameter of the barium sulfate particles is smaller than the above range, the stretching durability enhancement effect is insufficient, the viscosity of the paste is increased, and as a result, it becomes difficult to manufacture the paste.

The barium sulfate particles in the present invention is contained in an amount of 2 to 30% by mass, preferably 3 to 20% by mass, and more preferably 4 to 15% by mass relative to the total amount of the conductive particles and the barium sulfate particles. If the amount of the barium sulfate particles exceeds the above range, the electrical conductivity of the surface of the resulting coat lowers. On the other hand, if the amount of the barium sulfate particles is less than the above range, the stretching durability enhancement effect tends to be hardly developed.

It is preferred to use a flexible resin (c) as the resin in the present invention. As the flexible resin (c) in the present invention, thermoplastic resins, thermosetting resins, or rubbers having an elastic modulus of 1 to 1000 MPa can be given. In order to develop the film stretchability, rubbers are preferable. Examples of the rubbers include urethane rubber, acrylic rubber, silicone rubber, butadiene rubber, rubber containing a nitrile group such as nitrile rubber or hydrogenated nitrile rubber, isoprene rubber, vulcanized rubber, styrene-butadiene rubber, butyl rubber, chlorosulfonated polyethylene rubber, ethylene propylene rubber, vinylidene fluoride copolymer, and the like. Among these, rubber containing a nitrile group, chloroprene rubber, and chlorosulfonated polyethylene rubber are preferable, and rubber containing a nitrile group is particularly preferable. The elastic modulus in the present invention is preferably within a range of 3 to 600 MPa, more preferably 10 to 500 MPa, further preferably 30 to 300 MPa.

There is no particular limitation for the rubber containing a nitrile group as far as it is a rubber or elastomer containing a nitrile group, and nitrile rubber and hydrogenated nitrile rubber are preferable. Nitrile rubber is a copolymer of butadiene with acrylonitrile, and when the amount of bonding acrylonitrile increases, affinity with metal increases but rubber elasticity contributing to stretchability rather decreases. Therefore, the amount of bonding acrylonitrile in the acrylonitrile butadiene copolymer rubber is preferably 18 to 50% by mass, and more preferably 40 to 50% by mass.

Furthermore, the content of alkali metal in the flexible resin of the present invention is preferably 4000 ppm or less. By reducing the content of alkali metal, increase in viscosity with the passage of time due to pseudo crosslinkage of the conductive silver paste can be suppressed, and long-term storage stability is improved. Migration resistance of the formed conductive coat is also improved by reducing a metal ion source. Since the nitrile group having excellent affinity with silver powder preferentially adsorbs to the surface of the silver powder, the silver powder and the rubber containing a nitrile group in the coat do not become a fully homogeneous dispersed state, and uneven distribution or heterogeneity like a sea-island structure occurs. For this reason, even though the filling amount of the silver powder is small, an electrical conductivity network is easily formed. The rubber component increases by reducing the filling amount of the silver powder, whereby satisfactory elongation property and repetitive stretchability can be developed.

The flexible resin (c) in the present invention is contained in an amount of 7 to 35% by mass, preferably 9 to 28% by mass, and more preferably 12 to 20% by mass relative to the total amount of the conductive particles (a), the barium sulfate particles (b) and the flexible resin (c).

Furthermore, an epoxy resin may be blended to the conductive paste in the present invention. The epoxy resin in the present invention is preferably a bisphenol A type epoxy resin or a phenol novolac type epoxy resin. When blending an epoxy resin, a curing agent for the epoxy resin may be blended. As the curing agent, known amine compounds, polyamine compounds and the like can be used. The curing agent is preferably contained in an amount of 5 to 50% by mass, and more preferably 10 to 30% by mass relative to the epoxy resin. Moreover, the amount of the epoxy resin and the curing agent is 3 to 40% by mass, preferably 5 to 30% by mass, more preferably 8 to 24% by mass relative to the all resin components including the flexible resin.

The stretchable conductor composition of the present invention is obtained by kneading a mixture composed of the conductive particles (a), the barium sulfate particles (b) and the flexible resin (c). As a mixing method, a known apparatus, such as a kneader, an extruder or the like, for mixing and dispersing a mixture composed of a resin, a filler and the like in the production of a resin compound can be used, and mixing may be performed at a temperature at which the resin melts and flows.

When the flexible resin is a resin obtained through a latex, it is also possible to obtain a resin composition in such a manner that conductive particles and barium sulfate particles are added to a resin that is in a dispersed state before drying, these are mixed and dispersed in a liquid phase, and then dried. Of course, the mixture may be heated again after drying to make the resin in a molten state and further mixed and dispersed. After mixing and dispersing, the stretchable conductor composition can be prepared in an easy-to-handle form such as a pellet-like form, sheet-like form, or lump-like form.

In one embodiment according to the present invention, the stretchable conductor composition obtained as described above can be processed into a sheet-like form by a melt-molding method such as extrusion molding, press molding, roll molding or the like. The preferable thickness of the sheet is in the range of 5 µm to 1000 µm, more preferably 8 µm to 500 µm, further preferably 12 µm to 300 µm, and still further preferably 20 µm to 180 µm.

Kneading of a resin mixture is an industrially established method, but the amount of production per one process is relatively large. Therefore, when noble metal particles are used as conductive particles, a technique for obtaining the conductive resin composition in a smaller amount is required.

In the present invention, a solvent (d) is further added to the conductive particles (a), the barium sulfate particles (b), and the stretchable resin (c) constituting the resin composition, and these are mixed and dispersed with a disperser such as a dissolver, three-roll mill, rotation/revolution mixer, attritor, ball mill, sand mill or the like to form the resin composition into a paste, and the resulting paste is applied to a substrate and dried to obtain a resin composition.

The content of the solvent is not particularly limited since it should be appropriately investigated depending on the viscosity required of the paste, and it is generally preferred to be 30 to 80 in a mass ratio when the total mass of the conductive particles (a), the barium sulfate particles (b) and the flexible resin (c) is defined as 100.

As to the organic solvent used in the present invention, its boiling point is preferred to be equal to or higher than 100° C. and lower than 300° C., and more preferred to be equal to or higher than 130° C. and lower than 280° C. When the boiling point of the organic solvent is too low, the solvent may be evaporated during the paste production process and during use of the paste, and there is concern that the ratio of the ingredients constituting the conductive paste will be apt to change. On the other hand, when the boiling point of the organic solvent is too high, the amount of solvent remaining in the dried and cured coat becomes large, and hence there is concern that reliability of the coat will deteriorate.

Specific examples of the organic solvent using in the present invention include cyclohexanone, toluene, xylene, isophorone, γ-butyrolactone, benzyl alcohol, Solvesso 100, 150 and 200 (manufactured by Exxon Chemical), propylene glycol monomethyl ether acetate, terpineol, butyl glycol acetate, cliamylbenzene, triamylbenzene, n-dodecanol, cliethylene glycol, ethylene glycol monoethyl ether acetate, cliethylene glycol monoethyl ether acetate, cliethylene glycol monobutyl ether acetate, cliethylene glycol clibutyl ether, cliethylene glycol monoacetate, triethylene glycol diacetate, triethylene glycol, triethylene glycol monomethyl ether, triethylene glycol monoethyl ether, triethylene glycol monobutyl ether, tetraethylene glycol, tetraethylene glycol monobutyl ether, tripropylene glycol, tripropylene glycol monomethyl ether, and 2,2,4-trimethyl-1,3-pentanediol monoisobutyrate. As to a petroleum hydrocarbon, there may be exemplified AF Solvent No. 4, Solvesso No. 5, Solvesso No. 6 etc. manufactured by Nippon Oil Corporation. Note that the organic solvent may be used singly, or in combination of two or more thereof. Such organic solvents are appropriately contained such that a conductive silver paste has a viscosity suitable for printing or the like.

Into the paste for forming a stretchable conductor of the present invention, a known organic or inorganic additive such as a printability imparting agent, color tone adjusting agent, leveling agent, antioxidant, ultraviolet absorber, or the like can be blended as long as the contents of the invention are not impaired.

In one embodiment according to the present invention, a sheet of a stretchable conductor composition can be obtained by a solution film formation method in which the paste of the stretchable conductor composition obtained as described above is applied to a substrate, preferably a substrate having a molding release property, by a technique of a die coater, a squeegee coater, an applicator, a comma coater, screen printing or the like, and dried to form a sheet. This method is applicable to a low-amount production and also is a preferable method when a sheet with a relatively small thickness is required. The thickness of the sheet obtained through a paste state is preferably 1 μm to 300 μm, more preferably 3 μm to 200 μm, further preferably 5 μm to 120 μm, further more preferably 8 μm to 80 μm.

The sheet of the stretchable conductor composition of the present invention is formed from the stretchable conductor composition alone, but also can be formed so as to have an insulating layer on at least one surface of the sheet as required. Similar to the stretchable conductor, it is preferable that the insulating layer have stretchability. As a material of the insulating layer, a polymer material having a low elastic modulus is preferably used similar to the flexible resin constituting the stretchable conductor composition. When the sheet of the stretchable conductor composition is used as an electrical wiring, this insulating layer functions as an insulating layer between the stretchable conductor composition and the substrate and an adhesive layer to the substrate. In the case where the sheet is used as the electrical wiring, when the insulating layer is provided on the surface opposite to the substrate side, that is, on the surface of the electrical wiring, the insulating layer functions as an insulating coating layer.

The sheet of the stretchable conductor composition of the present invention can be formed into a sheet having a conductor composition layer containing carbon as a conductive filler on at least one surface of the sheet as necessary. This configuration is particularly preferable when the conductive particles used in the stretchable conductor composition are metal particles. Similarly, the resin material constituting the conductor composition containing carbon as a conductive filler is also preferably a polymer material having a low elastic modulus. Such a conductor composition layer containing carbon as a conductive filler functions as a contact material when the flexible conductor composition is used as an electrode.

A method for forming the insulating layer and/or the conductor composition layer containing carbon as a conductive filler on one or both surfaces of a flexible conductor composition sheet will be described below.

When a melt-molding method is employed as a method for producing a sheet, melt-molding may be repeatedly performed to sequentially stack sheets. Alternatively, it is also possible to simultaneously extrude a plurality of layers by using a two-layer die or a three-layer die to form into a sheet.

When a solution film formation method is employed, likewise, coating, drying and curing of the solution may be repeatedly performed to sequentially stack sheets. For example, a sheet can be stacked by a solution film formation method on a sheet formed by a melt-extrusion method, or reversely, a sheet may be stacked by a melt-extrusion method on a sheet formed by a solution film formation method. As a special case of the solution film formation method, a sheet having a multilayer structure can also be obtained by sequentially performing overprinting by a screen printing method or the like.

In the present invention, an insulating layer and/or a layer of a conductor composition containing carbon as a conductive filler can be formed in a predetermined pattern shape by a printing method such as a screen printing, stencil printing, or ink jet printing on a sheet formed by a melt-extrusion method or a solution film formation method. In this case, the insulating layer may function as an adhesive layer.

In the present invention, a stretchable conductor composition sheet, an insulating layer sheet, an adhesive sheet, a conductor composition sheet containing carbon as a conductive filler, and the like can be separately formed into a sheet, laminated and then used. For laminating, a known adhesive or hot-melt resin may be used. In addition, when each sheet maintains thermoplastic properties, it is possible to fuse and bond the sheets together.

Furthermore, in the present invention, the stretchable conductor resin composition sheet alone, preferably a sheet having the insulating layer and/or the layer of the stretchable conductor composition containing carbon as a conductive filler on at least one surface of the sheet is processed into a predetermined shape, and the processed sheet is attached to a garment or fabric that is raw fabric of a garment to form an electrical wiring.

A known adhesive or hot-melt type resin may be used for the attachment of the sheet to the fabric. An auxiliary material used for the attachment has preferably flexibility. The insulating layer sheet of the present invention may be turned to a B-stage state, which is a semi-dried and semi-cured state, and the insulating sheet itself may be used as a hot-melt material. In addition, the stretchable conductor resin composition layer may be turned to a B-stage state and attached to the fabric by applying heat/pressure.

EXAMPLES

Hereinafter, the invention will be explained in more detail and specifically by further showing examples. Evaluation results etc. of examples were measured by the following method.

<Amount of Nitrile>

The amount of nitrile was converted from the composition ratio obtained by analyzing the resulting resin material by NMR to a ratio by mass (% by mass) of monomer.

<Mooney Viscosity>

The measurement was conducted using SMV-300RT "Mooney Viscometer" manufactured by Shimadzu Corporation.

<Amount of Alkali Metal>

The resin was subjected to an ashing treatment, the resulting ash was extracted by means of hydrochloric acid, the contents of sodium and potassium were determined by atomic absorption spectrometry, and both contents were summed.

<Elastic Modulus>

The resin material was heated, compressed and molded into a sheet having a thickness of 200±20 μm, and then punched out into a dumbbell shape defined by ISO 527-2-1A to obtain a test piece. A tensile test was performed by the method defined in ISO 527-1 to determine an elastic modulus.

<Repeated Stretching Durability of Resin Material>

(1) Formation of Test Piece Sheet

A resin material was heated, compressed and molded into a sheet having a thickness of 200±20 μm, and then punched out into a dumbbell shape defined by ISO 527-2-1A to obtain a test piece.

(2) Stretching Test

An IPC bending tester manufactured by Yamashita Materials Corporation was modified, a reciprocating stroke of the tester was set to 13.2 mm, the test piece was fixed on a movable plate side with a clamp, the other end of the test piece was fixed to another fixed end with a clamp, and using a portion having a width of 10 mm and a length 80 mm in the dumbbell-shaped test piece, an effective length was adjusted to be 66 mm (corresponding to 20% elongation). Using the apparatus modified to enable a sample to be repeatedly stretched, stretching of the test piece was repeatedly performed 5000 times, and the durability to repeated stretching was evaluated by comparing the appearances before and after the test. A case where no change was found in the appearance as compared with the initial appearance was evaluated as "good", a case where cracks or the like were observed on the resin surface was evaluated as "poor".

<Repeated Stretching Durability of Stretchable Conductor Composition>

A sheet having a thickness of 80 μm was produced using the stretchable conductor composition by melt-molding or solution film formation, and then punched out into a dumbbell shape defined by ISO 527-2-1A to obtain a test piece.

An IPC bending tester manufactured by Yamashita Materials Corporation was modified, a reciprocating stroke of the tester was set to 13.2 mm, the test piece was fixed on a movable plate side with a clamp, the other end of the test piece was fixed to another fixed end with a clamp, and using a portion having a width of 10 mm and a length of 80 mm in the dumbbell-shaped test piece, an effective length was adjusted to be 66 mm (corresponding to 20% elongation). Using the apparatus modified to enable a sample to be repeatedly stretched, the sample was clipped with metal clips on portions wrapped with aluminum foil at 0 to 5 mm outside from both ends of the stretching effective length of 66 mm, and was repeatedly stretched while monitoring resistance values with the tester. The resistance values were read every 10 times until repeated stretching of 600 times, and in stretchings of more than 600 times, stretching was stopped every 50 times in a state of a stretching rate of 0%, a value after one minute after the stop was read and recorded, the number of times at the time when the resistance value had reached 100-fold of the initial value was recorded, and then the test was aborted.

<Electrical Conductivity (Sheet Resistance, Specific Resistance)>

The resistance value [Ω] of a part having a width of 10 mm and a length of 80 mm in the central portion of a dumbbell-shaped test piece defined by ISO 527-2-1A was measured using Milliohmmeter manufactured by Agilent Technologies, and a sheet resistance value "Ω square" was obtained by multiplying the measured resistance value by the aspect ratio (1/8) of the test piece.

Furthermore, by multiplying the resistance value [Ω] by a cross-sectional area (width of 1 [cm] mm×thickness [cm]) and then dividing by the length (8 cm), a specific resistance [Ωcm] was determined.

<Evaluation of Migration Resistance>

A stretchable conductor composition sheet having a thickness of 80 μm was cut into a 5 mm×100 mm sheet, and the cut out sheets were attached to a 100 mm×100 mm urethane sheet in parallel so as to have a space of 1.0 mm between the sheets to obtain a test piece. In a state where DC5V was applied between the electrodes of the test piece, deionized water was added dropwise between the conductors, and the time taken until the electrodes were short-circuited by dendritic precipitates was measured, and a case where the time was within 60 seconds was evaluated as "poor" and a case where the time was 60 seconds or longer was evaluated as "good". Note that the dropwise amount of deionized water was adjusted to an amount enough that water droplets cover in a width of 8 to 10 mm between the electrodes, and determination of short circuit was performed through visual observation.

11

<Surface Feeling>

Ten adults including five men and five women served as subjects, the printed surface was brought into contact with the skin of the abdomen of each of the subjects, and the sensory evaluation of texture was performed according to 5 grades from 5 points as "good feeling" to 1 point as "bad feeling". Averaging points of ten persons, a case of 4 or more points was evaluated as "very good", a case of 3 or more and less than 4 points was evaluated as "good", a case of 2 or more and less than 3 points was evaluated as "fair", a case of less than 2 points was evaluated as "poor".

<Average Particle Diameter>

The measurement was performed using a dynamic light-scattering particle size distribution analyzer LB-500 manufactured by Horiba, Ltd.

<Composition Analysis of Inorganic Particles>

Composition of inorganic particles to be used was analyzed using an X-ray fluorescence analyzer (X-ray fluorescence analyzer system 3270, manufactured by Rigaku Corporation) to examine Al components and Si components. Note that the amounts of coated Al and Si were obtained by converting the detected amount of metallic compounds of the Al components and the Si components into the amounts of the corresponding oxides (namely, Al components were calculated as $Al_2O_3$, Si components were calculated as $SiO_2$).

12

Next, in order to distill off unreacted monomers, the pressure in the reactor was first reduced, and then steam was introduced into the reactor to recover the unreacted monomers, thereby to obtain a synthetic rubber latex (L1) composed of NBR.

Sodium chloride and dilute sulfuric acid were added to the obtained latex, aggregation and filtration were performed. Then, deionized water in an amount 20 times in volume ratio to the resin was divided in five portions, the resin was washed by repeating redispersion in the deionized water and filtration, and dried in air to obtain a synthetic rubber resin R1.

The evaluation results of the obtained synthetic rubber resin R1 are shown in Table 1. The operations were similarly performed by changing raw materials, polymerization conditions, washing conditions, and the like to obtain resin materials R2 to R6 shown in Table 2. Abbreviations in the table are as follows:

NBR: acrylonitrile butadiene rubber

NBIR: acrylonitrile-isoprene rubber (isoprene: 10% by mass)

SBR: styrene-butadiene rubber (styrene/butadiene=50/50% by mass)

TABLE 1

|  | Latex | | | | | |
| --- | --- | --- | --- | --- | --- | --- |
|  | L1 | L2 | L3 | L4 | L5 | L6 |
| Stretchable resin | R1 | R2 | R3 | R4 | R5 | R6 |
| Component | NBR | NBR | NBIR | SBR | NBR | NBR |
| Polymerization temperature | 15 | 12 | 15 | 20 | 50 | 15 |
| Amount of nitrile [% by mass] | 43 | 35 | 26 | 0 | 39 | 42 |
| Amount of alkali metal [ppm] | 42 | 62 | 47 | 53 | 48 | 5600 |
| Mooney viscosity | 53 | 42 | 34 | 64 | 70 | 52 |
| Elastic modulus MPa | 31 | 25 | 21 | 63 | 147 | 33 |
| Washing | Washing | Washing | Washing | Washing | Washing | No Washing |
| Repeated stretching durability | good | good | good | good | good | good |

PRODUCTION EXAMPLE

<Polymerization of Synthetic Rubber Material>

The following materials were put into a stainless steel reactor equipped with a stirrer and a water cooling jacket and gently stirred while keeping the bath temperature at 15° C. by flowing nitrogen.

| | |
| --- | --- |
| butadiene | 54 parts by mass |
| acrylonitrile | 46 parts by mass |
| deionized water | 270 parts by mass |
| sodium dodecylbenzenesulfonate | 0.5 part by mass |
| sodium naphthalenesulfonate condensate | 2.5 parts by mass |
| t-dodecyl mercaptan | 0.3 part by mass |
| triethanolamine | 0.2 part by mass |
| sodium carbonate | 0.1 part by mass |

Next, an aqueous solution prepared by dissolving 0.3 part by mass of potassium persulfate in 19.7 parts by mass of deionized water was added dropwise into the reactor over 30 minutes, reaction was further continued for 20 hours, an aqueous solution prepared by dissolving 0.5 part by mass of hydroquinone in 19.5 parts by mass of deionized water was then added thereto, and an operation for stopping the polymerization reaction was carried out.

<Preparation of Barium Sulfate Particles (A)>

Warman Pump (inlet diameter: 40 mm, outlet diameter: 25 mm, internal volume: 850 mL, impeller rotation speed: 2380 rpm) was used as a reaction vessel. A sulfuric acid aqueous solution with a concentration of 110 g/L (1.1 mol/L) and a temperature of 30° C. was allowed to be sucked into this pump at a constant flow rate of 700 L/h. Simultaneously, a barium sulfide aqueous solution with a concentration of 120 g/L (0.71 mol/L) and a temperature of 50° C. was allowed to be sucked into the pump at a constant rate of 600 L/h to prepare 1000 mL of aqueous slurry (solid content: 95 g/L), and the slurry was heated to 60° C. Sodium silicate in an amount corresponding to 4.0 g of $SiO_2$ was diluted with 100 mL of pure water, and the mixture was added dropwise to the slurry over 20 minutes. Then, sodium aluminate in an amount corresponding to 2.0 g of $Al_2O_3$ was diluted with 100 mL of pure water and added dropwise to the slurry over 20 minutes. The reaction system was further heated to 70° C., and after stirring for 30 minutes, the slurry was neutralized with diluted sulfuric acid to pH 8 over 30 minutes. After further stirring for 10 minutes, the slurry was filtrated. The separated cake was washed thoroughly with water, and dried to give dried chips. The chips were crushed roughly, and then pulverized with an air current pulverizer. The obtained powder had a coated amount corresponding to 3.5% by mass of $SiO_2$ and 1.7% by mass of $Al_2O_3$ relative to the total amount of ultrafine barium sulfate particles that are base particles, and coated substances, and had the average particle diameter measured by a dynamic light scattering method of 0.3 μm.

<Preparation of Barium Sulfate Particles (B)>

Precipitated barium sulfate TS-1 manufactured by Takehara Kagaku Kogyo was used as barium sulfate particles (B). As a result of analyzing in the same manner as in the preparation of barium sulfate (A), the content of $SiO_2$ was 0.1% or less, and the content of $Al_2O_3$ was 0.1% or less. Therefore, these were judged not to be substantially contained. The average particle diameter determined by the same method was 0.6 μm.

<Preparation of Barium Sulfate Particles (C)>

Ground barite W-1 manufactured by Takehara Kagaku Kogyo was used as barium sulfate particles (C). The content of $SiO_2$ was 0.3% by mass, and the content of $Al_2O_3$ was 0.2% by mass. These were all judged as impurities because ground barite is derived from a natural product. The average particle diameter determined by the same method was 1.7 μm.

<Titanium Oxide Particles (D)>

Titanium oxide particles R-38L manufactured by Sakai Chemical Industry were used as titanium oxide particles (D). The average particle diameter was 0.4 μm. A list of the above-mentioned barium sulfate particles and titanium oxide particles is shown in Table 2.

TABLE 2

| Inorganic particles | | A Barium sulfate | B Barium sulfate | C Barium sulfate | D Titanium oxide |
|---|---|---|---|---|---|
| Particle diameter [μm] | | 0.3 | 0.6 | 1.7 | 0.4 |
| $SiO_2$ coating amount(detected amount) | % by mass | 3.5 | <0.1 | 0.3 | No analysis |
| $Al_2O_3$ coating amount(detected amount) | % by mass | 1.7 | <0.1 | 0.2 | No analysis |

[Preparation of Stretchable Conductor Composition Pellets]

The materials shown in Table 3 were premixed in a powder state, then charged in a melt extruder, mixed and taken out as pellets composed of a stretchable conductor composition. The temperature and mixing conditions were appropriately adjusted according to the flexible resin used.

[Preparation of Stretchable Conductor Composition Sheet]

The obtained pellets were spread over an iron plate whose surface was processed with hard chrome, and heat and pressure were applied thereon with a vacuum press to obtain a sheet having a thickness of 80 μm. The evaluation results for the obtained sheet are shown in Table 3-1 and Table 3-2.

Note that in Table 3-1 and Table 3-1, amorphous silver powder 1 is an aggregated silver powder G-35 (average particle diameter: 6.0 μm) manufactured by DOWA Electronics, and amorphous silver powder 2 is an aggregated silver powder having an average particle diameter of 2.1 μm obtained by wet-classifying the aggregated silver powder G-35 manufactured by DOWA Electronics.

TABLE 3-1

| Stretchable conductor composition sheet | | Example 1 S1 | Example 2 S2 | Example 3 S3 | Example 4 S4 | Example 5 S5 | Example 6 S6 | Example 7 S7 | Example 8 S8 |
|---|---|---|---|---|---|---|---|---|---|
| Stretchable resin (R1) | parts by mass | 12.0 | — | — | — | — | 12.0 | 12.0 | 12.0 |
| Stretchable resin (R2) | parts by mass | — | 12.0 | — | — | — | — | — | — |
| Stretchable resin (R3) | parts by mass | — | — | 12.0 | — | — | — | — | — |
| Stretchable resin (R4) | parts by mass | — | — | — | 12.0 | — | — | — | — |
| Stretchable resin (R5) | parts by mass | — | — | — | — | 12.0 | — | — | — |
| Stretchable resin (R6) | parts by mass | — | — | — | — | — | — | — | — |
| Isophorone | parts by mass | — | — | — | — | — | — | — | — |
| Scalelike silver powder | parts by mass | 52.0 | — | — | — | — | 52.0 | 52.0 | 56.0 |
| Amorphous silver powder 1 | parts by mass | — | 52.0 | 52.0 | 52.0 | 52.0 | — | — | — |
| Amorphous silver powder 2 | parts by mass | — | — | — | — | — | — | — | — |
| Barium sulfateA | parts by mass | 6.0 | 6.0 | 6.0 | 6.0 | 6.0 | — | — | 2.0 |
| Barium sulfateB | parts by mass | — | — | — | — | — | 6.0 | — | — |
| Barium sulfateC | parts by mass | — | — | — | — | — | — | 6.0 | — |
| Titanium oxideD | parts by mass | — | — | — | — | — | — | — | — |
| Specific resistance | Ω cm | $7 \times 10^{-4}$ | $5 \times 10^{-4}$ | $7 \times 10^{-4}$ | $6 \times 10^{-4}$ | $6 \times 10^{-4}$ | $1.5 \times 10^{-3}$ | $2 \times 10^{-3}$ | $3 \times 10^{-4}$ |
| Migration resistance | | good | good | good | good | good | good | good | good |
| Repeated stretching durability (time) | | 2300 | 2400 | 1100 | 1400 | 3050 | 1100 | 800 | 1550 |
| Surface feeling | | good | good | good | good | good | good | fair | good |

TABLE 3-2

| Stretchable conductor composition sheet | Example 1 S1 | Example 2 S2 | Example 3 S3 | Example 4 S4 | Example 5 S5 | Example 6 S6 | Example 7 S7 | Example 8 S8 |
|---|---|---|---|---|---|---|---|---|
| Stretchable resin(R1) parts by mass | 12.0 | — | — | — | — | 12.0 | 12.0 | 12.0 |
| Stretchable resin(R2) parts by mass | — | 12.0 | — | — | — | — | — | — |
| Stretchable resin(R3) parts by mass | — | — | 12.0 | — | — | — | — | — |
| Stretchable resin(R4) parts by mass | — | — | — | 12.0 | — | — | — | — |
| Stretchable resin(R5) parts by mass | — | — | — | — | 12.0 | — | — | — |
| Stretchable resin(R6) parts by mass | — | — | — | — | — | — | — | — |

TABLE 3-2-continued

| | | | | | | | | | |
|---|---|---|---|---|---|---|---|---|---|
| Isophorone | parts by mass | — | — | — | — | — | — | — | — |
| Scalelike silver powder | parts by mass | 52.0 | — | — | — | — | 52.0 | 52.0 | 52.0 |
| Amorphous silver powder 1 | parts by mass | — | 52.0 | 52.0 | 52.0 | 52.0 | — | — | — |
| Amorphous silver powder 2 | parts by mass | — | — | — | — | — | — | — | — |
| Barium sulfateA | parts by mass | 6.0 | 6.0 | 6.0 | 6.0 | 6.0 | — | — | 2.0 |
| Barium sulfateB | parts by mass | — | — | — | — | — | 6.0 | — | — |
| Barium sulfateC | parts by mass | — | — | — | — | — | — | 6.0 | — |
| Titanium oxideD | parts by mass | — | — | — | — | — | — | — | — |
| Specific resistance | Ω cm | $7 \times 10^{-4}$ | $5 \times 10^{-4}$ | $7 \times 10^{-4}$ | $6 \times 10^{-4}$ | $6 \times 10^{-4}$ | $1.5 \times 10^{-3}$ | $2 \times 10^{-3}$ | $3 \times 10^{-4}$ |
| Migration resistance | | good | good | good | good | good | good | good | good |
| Repeated stretching durability (time) | | 2300 | 2400 | 1100 | 1400 | 3050 | 1100 | 800 | 1550 |
| Surface feeling | | good | good | good | good | good | good | fair | good |

| Stretchable conductor composition sheet | | Example 9 S9 | Example 10 S10 | Example 11 S11 | Example 12 S12 | Example 13 S13 | Example 14 S14 | Example 15 S15 | Example 16 S16 |
|---|---|---|---|---|---|---|---|---|---|
| Stretchable resin(R1) | parts by mass | 12.0 | 12.0 | — | — | 12.0 | 12.0 | — | — |
| Stretchable resin(R2) | parts by mass | — | — | 6.0 | — | — | — | — | — |
| Stretchable resin(R3) | parts by mass | — | — | — | — | — | — | 12.0 | — |
| Stretchable resin(R4) | parts by mass | — | — | — | 12.0 | — | — | — | — |
| Stretchable resin(R5) | parts by mass | — | — | 6.0 | — | — | — | — | — |
| Stretchable resin(R6) | parts by mass | — | — | — | 12.0 | — | — | — | — |
| Isophorone | parts by mass | — | 10.0 | — | — | — | — | — | — |
| Scalelike silver powder | parts by mass | 54.0 | 43.0 | — | — | 52.0 | 58.0 | 58.0 | — |
| Amorphous silver powder 1 | parts by mass | — | — | — | 52.0 | — | — | — | 58.0 |
| Amorphous silver powder 2 | parts by mass | — | — | 52.0 | — | — | — | — | — |
| Barium sulfateA | parts by mass | 4.0 | 15.0 | 6.0 | 6.0 | — | — | — | — |
| Barium sulfateB | parts by mass | — | — | — | — | — | — | — | — |
| Barium sulfateC | parts by mass | — | — | — | — | — | — | — | — |
| Titanium oxideD | parts by mass | — | — | — | — | 6.0 | — | — | — |
| Specific resistance | Ω cm | $7 \times 10^{-4}$ | $1 \times 10^{-3}$ | $4 \times 10^{-4}$ | $8 \times 10^{-4}$ | $4 \times 10^{-2}$ | $1 \times 10^{-3}$ | $6 \times 10^{-4}$ | $8 \times 10^{-4}$ |
| Migration resistance | | good | good | good | good | good | good | good | good |
| Repeated stretching durability (time) | | 2100 | 1550 | 3900 | 2300 | 40 | 550 | 380 | 350 |
| Surface feeling | | good | fair | good | good | poor | fair | fair | fair |

[Preparation of Conductive Paste]

Examples, in which components of a stretchable conductor composition are made into a paste thereinafter the paste is made into a sheet, will be described below.

1.5 parts by mass of a liquid bisphenol-A based epoxy resin with an epoxy equivalent of 175 to 195, 10 parts by mass of the stretchable resin (R1) obtained in the production example, and 0.5 part by mass of the latent curing agent [trade name: Amicure PN23 manufactured by Ajinomoto Fine Chemical Co., Ltd.] were mixed and stirred with 30 parts by mass of isophorone to be dissolved, thereby to obtain a binder resin composition A1. Next, 58.0 parts by mass of fine flaky silver powder [trade name: Ag-XF301 manufactured by Fukuda Metal Foil & Powder Co., Ltd.] having an average particle diameter of 6 μm was added to the binder resin composition A1, uniformly mixed and dispersed by a three-roll mill to obtain a conductive paste C1. The evaluation results of the obtained conductive paste C1 are shown in Table 2.

Then, blending was carried out by changing the materials to obtain conductive pastes C2 to C16 as shown in Table 4-1 and Table 4-2. Likewise, the evaluation results are shown in Table 4-1 and Table 4-2.

Note that in Table 4-1 and Table 4-1, amorphous silver 1 is an aggregated silver powder G-35 (average particle diameter: 6.0 μm) manufactured by DOWA Electronics, and amorphous silver 2 is an aggregated silver powder (average particle diameter: 2.1 μm) obtained by wet-classifying the aggregated silver powder G-35 manufactured by DOWA Electronics.

TABLE 4-1

| | Conductive paste | | Example 13 C1 | Example 14 C2 | Example 15 C3 | Example 16 C4 | Example 17 C5 | Example 18 C6 | Example 19 C7 | Example 20 C8 |
|---|---|---|---|---|---|---|---|---|---|---|
| Formulation | Epoxy resin*) | parts by mass | 1.5 | — | 1.5 | — | — | — | — | 1.5 |
| | Stretchable resin (R1) | parts by mass | 10.0 | — | — | — | — | 12.0 | 12.0 | 10.0 |
| | Stretchable resin (R2) | parts by mass | — | 12.0 | — | — | — | — | — | — |
| | Stretchable resin (R3) | parts by mass | — | — | 10.0 | — | — | — | — | — |
| | Stretchable resin (R4) | parts by mass | — | — | — | 12.0 | — | — | — | — |
| | Stretchable resin (R5) | parts by mass | — | — | — | — | 12.0 | — | — | — |
| | Stretchable resin (R6) | parts by mass | — | — | — | — | — | — | — | — |
| | Curing agent | parts by mass | 0.5 | — | 0.5 | — | — | — | — | 0.5 |
| | Isophorone | parts by mass | 30.0 | 30.0 | 30.0 | 30.0 | 30.0 | 30.0 | 30.0 | 30.0 |
| | Scalelike silver powder | parts by mass | 52.0 | 52.0 | 52.0 | — | — | 52.0 | 52.0 | 56.0 |

TABLE 4-1-continued

|  |  | Example 13 C1 | Example 14 C2 | Example 15 C3 | Example 16 C4 | Example 17 C5 | Example 18 C6 | Example 19 C7 | Example 20 C8 |
| --- | --- | --- | --- | --- | --- | --- | --- | --- | --- |
| Conductive paste |  |  |  |  |  |  |  |  |  |
| Amorphous silver powder 1 | parts by mass | — | — | — | 52.0 | 52.0 | — | — | — |
| Amorphous silver powder 2 | parts by mass | — | — | — | — | — | — | — | — |
| Barium sulfate A | parts by mass | 6.0 | 6.0 | 6.0 | 6.0 | 6.0 | — | — | 2.0 |
| Barium sulfate B | parts by mass | — | — | — | — | — | 6.0 | — | — |
| Barium sulfate C | parts by mass | — | — | — | — | — | — | 6.0 | — |
| Titanium oxide D | parts by mass | — | — | — | — | — | — | — | — |
| Specific resistance | Ω cm | $5 \times 10^{-4}$ | $4 \times 10^{-4}$ | $5 \times 10^{-4}$ | $5 \times 10^{-4}$ | $7 \times 10^{-4}$ | $1 \times 10^{-3}$ | $2 \times 10^{-3}$ | $7 \times 10^{-4}$ |
| Migration resistance |  | good | good | good | good | good | good | good | good |
| Repeated stretching durability (time) |  | 2500 | 2550 | 1200 | 1450 | 3150 | 1000 | 850 | 1800 |
| Surface feeling |  | good | good | good | good | good | good | fair | good |

TABLE 4-2

|  |  |  | Example 21 C9 | Example 22 C10 | Example 23 C11 | Example 24 C12 | Comparative Example 5 C13 | Comparative Example 6 C14 | Comparative Example 7 C15 | Comparative Example 8 C16 |
| --- | --- | --- | --- | --- | --- | --- | --- | --- | --- | --- |
|  | Conductive paste |  |  |  |  |  |  |  |  |  |
| Formulation | Epoxy resin*1) | parts by mass | 1.5 | 1.5 | — | — | — | — | — | — |
|  | Stretchable resin (R1) | parts by mass | 10.0 | 10.0 | — | — | 12.0 | 12.0 | — | — |
|  | Stretchable resin (R2) | parts by mass | — | — | 6.0 | — | — | — | — | — |
|  | Stretchable resin (R3) | parts by mass | — | — | — | — | — | — | 12.0 | — |
|  | Stretchable resin (R4) | parts by mass | — | — | — | — | — | — | — | 12.0 |
|  | Stretchable resin (R5) | parts by mass | — | — | 6.0 | — | — | — | — | — |
|  | Stretchable resin (R6) | parts by mass | — | — | — | 12.0 | — | — | — | — |
|  | Curing agent | parts by mass | 0.5 | 0.5 | — | — | — | — | — | — |
|  | Isophorone | parts by mass | 30.0 | 30.0 | 30.0 | 30.0 | 30.0 | 30.0 | 30.0 | 30.0 |
|  | Scalelike silver powder | parts by mass | 54.0 | 43.0 | — | — | 52.0 | 58.0 | 58.0 | — |
|  | Amorphous silver powder 1 | parts by mass | — | — | — | — | — | — | — | — |
|  | Amorphous silver powder 2 | parts by mass | — | — | 52.0 | — | — | — | — | 58.0 |
|  | Barium sulfate A | parts by mass | 4.0 | 15.0 | 6.0 | 6.0 | — | — | — | — |
|  | Barium sulfate B | parts by mass | — | — | — | — | — | — | — | — |
|  | Barium sulfate C | parts by mass | — | — | — | — | — | — | — | — |
|  | Titanium oxide D | parts by mass | — | — | — | — | 6.0 | — | — | — |
|  | Specific resistance | Ω cm | $6 \times 10^{-4}$ | $1 \times 10^{-3}$ | $3 \times 10^{-4}$ | $6 \times 10^{-4}$ | $3 \times 10^{-2}$ | $7 \times 10^{-4}$ | $5 \times 10^{-4}$ | $7 \times 10^{-4}$ |
|  | Migration resistance |  | good | good | good | poor | good | good | good | good |
|  | Repeated stretching durability (time) |  | 2200 | 1700 | 4500 | 2350 | 20 | 530 | 350 | 320 |
|  | Surface feeling |  | good | fair | good | good | poor | fair | fair | fair |

Application Example 1

The stretchable conductor composition sheet cut into a length of 190 mm and a width of 10 mm obtained in Example 1 was stacked on the central portion of a hot-melt urethane sheet (first insulating layer) having a length of 200 mm and a width of 30 mm, and a polyurethane sheet (cover coat layer) having a length of 150 mm and a width of 25 mm was further stacked thereon such that 20 mm of each end of the stretchable conductor composition sheet was exposed.

Next, a 2-way tricot fabric ("KNZ2740" manufactured by GUNSEN, nylon yarn:urethane yarn=63% by mass:37% by mass (blend ratio), areal weight: 194 g/m²) having a length of 210 mm and a width of 50 mm was stacked so as to be in contact with the above-mentioned first insulating layer, and all of these were bonded using a hot press to obtain a stretchable conductor composition sheet laminated on the fabric.

Repeated stretching durability (number of times) for the obtained sheet sample was determined in the same manner as in Example 1. As a result, the sheet sample exhibited excellent properties of repeated stretching durability of 2500 times.

Application Example 2

In the same manner as in Application Example 1, a circular electrode having a diameter 50 mm was formed from the stretchable conductor composition sheet on the intersection of each of left and right posterior axillary lines and the seventh rib, and a stretchable conductor composition sheet wiring having a width of 10 mm was formed from each of the circular electrodes to the center of the chest on the inside of a sports shirt. The contour line of the joint between the electrode portion and the wiring portion contour line was smoothly processed with an R10 mm. Note that the wirings extending from the left and right electrodes to the center of the chest have a gap of 5 mm therebetween at the center of the chest, and both wirings were not short-circuited. The first insulating layer was made 5 mm larger than the outline of the stretchable conductor composition sheet. The cover coat layer of the wiring portion had a width of 16 mm and a size enough to cover up to 3 mm outside from the stretchable conductor composition sheet, and the edge 10 mm on the chest center side of the wiring formed from the stretchable conductor composition sheet was not covered with the cover coat layer. The cover coat layer of the electrode portion was covered concentrically with the electrode and in a ring shape having an inner diameter of 44 mm and an outer diameter of 56 mm, and the joint between the electrode portion and the wiring portion was also covered up to 3 mm outside.

Subsequently, a stainless steel hook was attached on a surface side of the sport shirt at the edge of the center of the chest where no cover coat layer of the left and right wiring portions was disposed, and in order to ensure electrical continuity with the wiring portion on a back side of the surface, the stainless steel hook was electrically connected to the stretchable conductor composition layer using a conductive yarn in which a fine metal wire was twisted.

Heart rate sensor WHS-2 manufactured by Union Tool Co. was connected via the stainless steel hook, and was programed so that a heart rate data could be received with a smartphone manufactured by Apple on which the application "myBeat" designed specifically for the heart rate sensor WHS-2 had been installed to be displayed on its screen. In this way, the sports shirt in which a heart rate measurement function was incorporated was produced.

This shirt was worn by a subject, and electrocardiogram data of the subject was acquired during being at rest, walking, running, riding a bicycle, driving a car, and sleeping. The acquired electrocardiogram data had less noise and a high resolution, and hence had a quality as an electrocardiogram that is capable of analyzing mental states, physical condition, fatigue, sleepiness, stress levels, or the like can be analyzed from the change in heart rate interval, the electrocardiogram waveform, and the like.

Likewise, using the stretchable conductor composition sheets of Example 5, Example 6, Example 7, Example 11, and Comparative Example 1, sports shirts in which a heart rate measurement function was incorporated were obtained in the same manner as above. As a result, each of the Examples could acquire excellent electrocardiogram data except that as for the stretchable conductor composition of Example 7, noise was occasionally observed when running, and as for the stretchable conductor composition of Comparative Example 1, it was impossible to measure the heart rate because of disturbed waveforms during rigorous running. The obtained results corresponded to the quality of the surface feeling of the stretchable conductor composition. It was assumed that the surface feeling relates to roughness of the surface, and it was suggested that particularly when the subject severely moves, the contact between the subject's body surface and the electrode surface may become poor.

Application Example 3

The conductive paste obtained in Example 13 was applied onto a release sheet and dried in a hot-air drying oven of 120° C. for 30 minutes or longer to produce a sheet-like stretchable conductor layer with a release sheet having a thickness of 45 μm.

Next, a polyurethane hot-melt sheet was laminated on the conductive sheet with a release sheet using a hot press, and then punched out in a length of 190 mm and a width of 10 mm to obtain a three-layer sheet having a configuration of release sheet/stretchable conductor composition/polyurethane hot-melt sheet.

Next, the obtained three-layer sheet was stacked on the center portion of a 2-way tricot fabric ("KNZ2740" manufactured by GUNSEN, nylon yarn:urethane yarn=63%:37% (blend ratio), areal weight: 194 g/m$^2$) having a length of 200 mm and a width of 30 mm such that the hot-melt sheet side of the three-layer sheet was in contact with the fabric, and they were bonded using a hot press to obtain a stretchable electrode sheet. A hot-melt urethane sheet having a length of 150 mm and a width of 25 mm was further stacked on the stretchable conductor composition layer of the stretchable electrode sheet such that 20 mm of both ends of the stretchable conductor composition layer was each exposed, and they were bonded using a hot press. Furthermore, the exposed portion of the stretchable conductor composition layer was coated with a stretchable carbon paste by screen printing so as to be covered with a rectangle having a length of 22 mm and a width of 14 mm to obtain a stretchable composite electrode sheet.

The obtained stretchable composite sheet was punched out in a length of 194 mm and a width of 14 mm so as not to cut across the stretchable conductor composition layer, and the punched out sheet was bonded on a region from a side portion to a center portion on the rear side of the cup under part of sports brassiere using a hot-melt sheet in such a manner that the carbon paste coating layer faced a skin side. The carbon paste coating layer on the side portion serves as an electrode portion in contact with a body. A stainless steel hook was attached on the outer side corresponding to each of the left and right carbon paste coating portions opposing to the center portion of the brassiere, and electrically connected to the stretchable conductor composition layer using a conductive yarn in which a fine metal wire was twisted. Heart rate sensor WHS-2 manufactured by Union Tool Co. was connected via the stainless steel hook, and was programed so that a heart rate data could be received with a smartphone manufactured by Apple on which the application "myBeat" designed specifically for the heart rate sensor WHS-2 had been installed and to be displayed on its screen. In this way, the sports brassiere in which a heart rate measurement function was incorporated was produced.

This sports brassiere was worn by a subject, and electrocardiogram data of the subject was acquired during being at rest, walking, running, riding a bicycle, driving a car, and sleeping. The acquired electrocardiogram data had less noise and a high resolution, and hence had a quality as an electrocardiogram that is capable of analyzing mental states, physical condition, fatigue, sleepiness, stress levels, or the like from the change in heart rate interval, the electrocardiogram waveform, and the like.

Likewise, sports brassieres in which a heart rate measurement function was incorporated were produced in the same manner as above except that the pastes of Examples 14, 16, 17 and 23 were used. As a result, each of the Examples could acquire excellent electrocardiogram data.

Application Example 4

A cover coat layer composed of urethane resin having stretchability was formed on a release sheet, a stretchable carbon paste was then formed on a portion corresponding to an electrode by screen printing, and dried and cured. Next, a paste composed of the stretchable conductor composition obtained in Example 17 was overlaid and printed thereon, and dried and cured. Further thereon, a urethane resin layer having hot-melt property was similarly overlaid and printed by screen printing. The pattern of the stretchable conductor composition layer is shown in the drawing. The portion on which the carbon paste was overlaid is a portion having a wiring length of 15 mm at the end of a wrist side.

The urethane sheet having hot-melt property side of the resulting overlaid printed product was laminated on the back side of a fabric glove, and the wiring was transferred from the release sheet to the glove using a hot press to obtain a glove with a wiring. Lead wires were attached to the electrodes in a portion corresponding to a wrist of the obtained glove with a wiring by using a conductive adhesive to achieve such a configuration that the resistance change of the wiring in accordance with bending of each finger joint can be read by a multichannel resistance meter.

Using the obtained device configuration, first, a user wore a glove type input device on the right hand, a resistance value of a portion corresponding to each finger joint in a state where the user opens the hand, which is a state of "paper" of scissors-paper-rock, was set as an initial value, and a resistance value in a state where the user holds the hand, which is a state of "rock" of scissors-paper-rock, was set as a limit value. A range of change in resistance of each finger joint between these two states was divided into 64 gradations, by bring the 64 gradations into correspondence with bending states of finger joints, a three-dimensional image of CG-synthesized fingers by software was operated.

The movement of the resulting CG fingers was natural, smooth and excellent. In addition, it was also possible to replicate complex movement such as "scissors-paper-rock" and fingerspelling.

Reference Example

Preparation of Stretchable Carbon Paste 24 parts by mass of the stretchable resin (R1), 4 parts by mass of Ketjenblack, and 30 parts by mass of isophorone were preliminarily stirred and then kneaded and dispersed by a three-roll mill to obtain a stretchable carbon paste (C17).

Reference Example

Stretchable Resin Ink (Resin Ink for Cover Coat)

7.5 parts by mass of epoxy resin, 30 parts by mass of the stretchable resin (R2) and 0.5 parts by mass of a curing agent were mixed and dissolved in 30 parts by mass of isophorone to obtain a stretchable resin ink (C18) for a cover coat.

Application Example 5

A rectangular pattern having a width of 50 mm and a length of 450 mm between the front hem portion and the front collar portion of a knitted sportswear (shirt) was coated with a water-dispersible urethane resin so as to have a dry areal weight of 50 g/m$^2$, followed by drying and curing to form a urethane underlayer. Next, two wirings having a width of 10 mm and a length of 430 mm were formed on the urethane resin layer by screen printing using the conductive paste C2 obtained in Example 14 so as to be placed such that a distance from the edge of the urethane underlayer was about 10 mm and so as to have a dry film thickness of 28 µm, and then dried and cured at 120° C. for 30 minutes in a drying oven to obtain a sports shirt with a wiring. 15 mm of the hem portion and 15 mm of the collar portion of the obtained wirings were each covered with a masking tape, and the wiring portion was provided with insulation by coating with a water-dispersible urethane and further drying. Then, the masking tape was peeled off, and the part that had been covered with the masking tape was subjected to printing with the carbon paste C17 by a screen printing method so that a dry film thickness became 15 µm, followed by drying and curing at 120° C. for 20 minutes to obtain an electrode portion.

Stainless steel hooks were sewn on the hem portion and the collar portion of the electrode thus obtained of the sports shirt with a wiring using a sewing thread and a conductive thread in combination, and a detachable mini pin jack was attached using the hooks of both the hem and collar portions.

When a headphone stereo was connected via the sports shirt having the mini pin jack, it was possible to listen to music reproduced with good sound quality both during being at rest and during jogging.

Application Example 6

A synthetic leather glove was placed on a flat hand-shaped plate made of a plastic plate having a thickness of 5 mm so as not to make wrinkles. Using a screen printing machine, the conductive paste (C11) obtained in Example 23 was applied to the glove to print a conductive pattern shown in the drawing. Subsequently, drying was performed at 100° C. for 120 minutes to obtain a glove with a wiring. Lead wires were attached to the electrodes in a portion corresponding to a wrist of the obtained glove with a wiring by using a conductive adhesive to achieve such a configuration that the resistance change of the wiring in accordance with bending of each joint can be read by a multichannel resistance meter.

Using the obtained device configuration, first, a user wore a glove type input device on the right hand, a resistance value of a portion corresponding to each joint of the hand in an opened state, which is a state of "paper" of scissors-paper-rock, was set as an initial value, and a resistance value of that of the hand in a closed state, which is a state of "rock" of scissors-paper-rock, was set as a limit value. A range of change in resistance of each joint between these two states was divided into 64 gradations, and by bring the 64 gradations into correspondence with the bending and stretching states of joints, a three-dimensional image of fingers CG-synthesized by software was operated.

The movement of the resulting CG fingers was natural, smooth and excellent. In addition, it was also possible to replicate complex movement such as "scissors-paper-rock" and fingerspelling.

Application Example 7

First, a predetermined pattern was printed on a release PET film having a thickness of 125 µm using the stretchable insulating resin ink (C18) for forming a cover coat layer, dried and cured. The pattern corresponded to a land section that covers the periphery of an electrode portion in a ring shape and an insulating coating section that covers the electrical wiring portion composed of the stretchable conductor. The land section covered the outer circumference 3 mm of an electrode pattern described later, and had a ring width of 5 mm. The insulating coating section had a width of 16 mm and covered the stretchable conductor having a width of 10 mm. The dry thickness of the cover coat layer was adjusted to be 20 µm.

Next, using the stretchable carbon paste (C17), printing was performed on a portion to be an electrode portion, followed by drying and curing. The electrode portion was a circle having a diameter of 50 mm arranged concentrically with the ring of the previously printed cover coat layer. This stretchable carbon paste was prepared in such a manner that barium sulfate particles were removed from the paste for forming a stretchable conductor of Example 3, 12 parts by weight of Ketjenblack was further added thereto instead of silver powder which is a conductive filler, and the resulting mixture was kneaded and dispersed. The dry film thickness of the stretchable carbon paste layer was 15 µm.

Next, the electrode portion and the electrical wiring portion were printed using the paste C5 for forming a stretchable conductor obtained in Example 17, which is to be a stretchable conductor. The electrode portion had a circular shape with a diameter of 50 mm, and was arranged concentrically with the ring-shaped land section. The electrical wiring portion had a width of 10 mm. The dry thickness of the stretchable conductor portion was adjusted to be 50 μm by repeating the process from printing to drying.

Furthermore, using the stretchable insulating resin ink used for the cover coat layer, printing was performed so as to cover all the printed patterns including the cover coat layer, and a weak drying operation was performed at 60° C. for 10 minutes so that the solvent was intentionally left and tackiness remained to obtain a transferable printed electrode wiring sheet.

Subsequently, the transferable printed electrode wiring obtained by the above processes was overlaid on a predetermined portion of the sports shirt turned inside out and hot-pressed to transfer the printed matter from the release PET film to the sports shirt, followed by drying at 115° C. for 30 minutes, whereby a sports shirt with an electrical wiring was obtained.

In the obtained sports shirt with an electrical wiring, the circular electrode having a diameter 50 mm was placed on the intersection of each of left and right posterior axillary lines and the seventh rib, and the electrical wiring composed of the stretchable conductor composition having a width of 10 mm was formed from each of the circular electrodes to the center of the chest on the inside of the sports shirt. The wirings extending from the left and right electrodes to the center of the chest had a gap of 5 mm therebetween at the center of the chest, and both wirings were not short-circuited.

Subsequently, a stainless steel hook was attached on a surface side of the sports shirt at the edge of the center of the chest where no cover coat layer of the left and right wiring portions was disposed, and in order to ensure electrical continuity with the wiring portion on a back side of the surface, the stainless steel hook was electrically connected to the stretchable conductor composition layer using a conductive yarn in which a fine metal wire was twisted.

Heart rate sensor WHS-2 manufactured by Union Tool Co. was connected via the stainless steel hook, and was programed so that a heart rate data could be received and displayed with a smartphone manufactured by Apple in which the application "myBeat" designed specifically for the heart rate sensor WHS-2 had been installed. In this way, the sports shirt in which a heart rate measurement function was incorporated was produced.

This shirt was worn by a subject, and electrocardiogram data of the subject was acquired during being at rest, walking, running, riding a bicycle, driving a car, and sleeping. The acquired electrocardiogram data had less noise and a high resolution, and hence had a quality as an electrocardiogram that is capable of analyzing mental states, physical condition, fatigue, sleepiness, stress levels, or the like from the change in heart rate interval, the electrocardiogram waveform, and the like.

INDUSTRIAL APPLICABILITY

As described above, by using the paste for forming a stretchable conductor of the present invention and the stretchable conductor obtained from the paste in a wiring and an electrode material, it is possible to form an electrical wiring by a printing method directly and indirectly on garments and textile products made of stretchable textile, fabric or the like. The electrical wiring on the textile product obtained by using the stretchable conductor of the present invention is applicable, without being limited to the use examples shown in the above application examples, to a wearable device for detecting information of a human body such as bioelectric potential including myoelectric potential and cardiac potential, and biological information including body temperature, pulse, blood pressure, and the like with a sensor or the like provided in a garment; a garment incorporating an electric heating device; a wearable device incorporating a sensor for measuring a clothing pressure; wear that measures a body size by using a clothing pressure; a sock-type device for measuring a pressure of a sole of foot; a garment in which flexible solar cell modules are integrated in textiles; a wiring part of a tent, bag or the like; a low frequency treatment apparatus having a joint part; a wiring part of a thermal treatment apparatus or the like; a sensing part of degree of flexion, and the like. Such wearable devices can be used for not only a human body but also an animal such as pet or livestock, can be applied to a mechanical device having an expandable portion, a bending portion, and the like, and can also be used as an electrical wiring of a system that is used by connecting a mechanical device such as a robotic prosthetic arm or leg to a human body. In addition, it is also useful as a wiring material for an implant device to be embedded in the body.

The invention claimed is:

1. A stretchable conductor composition comprising at least
    conductive particles (a),
    barium sulfate particles (b), and
    a flexible resin (c) having a tensile elastic modulus of 1 MPa or more and 1000 MPa or less,
    wherein the barium sulfate particles (b) are contained in an amount of 2 to 30% by mass relative to the total amount of the conductive particles (a) and the barium sulfate particles (b), and the flexible resin (c) is contained in an amount of 7 to 35% by mass relative to the total amount of the conductive particles (a), the barium sulfate particles (b) and the flexible resin (c).

2. The stretchable conductor composition according to claim 1,
    wherein the average particle diameter of the conductive particles as measured by a dynamic light scattering method is larger than the average particle diameter of the barium sulfate particles as measured by a dynamic light scattering method.

3. The stretchable conductor composition according to claim 1,
    wherein the barium sulfate particles are subjected to a surface treatment with a hydroxide and/or oxide of one or both of Al and Si.

4. The stretchable conductor composition according to claim 1,
    wherein the conductive particles comprise silver particles having an average particle diameter, as measured by a dynamic light scattering method, of 0.5 to 20 μm.

5. A garment comprising an electrical wiring comprising the stretchable conductor composition according to claim 1.

6. A method for producing the garment comprising a wiring comprising a stretchable conductor composition according to claim 5, the method comprising:
   printing an electrical wiring directly on a fabric by using a paste for forming a stretchable conductor, said paste comprising at least
   conductive particles (a),
   barium sulfate particles (b),
   a flexible resin (c) having a tensile elastic modulus of 1 MPa or more and 1000 MPa or less, and
   a solvent (d),
   wherein the barium sulfate particles (b) are contained in an amount of 2 to 30% by mass relative to the total amount of the conductive particles (a) and the barium sulfate particles (b), and the flexible resin (c) is contained in an amount of 7 to 35% by mass relative to the total amount of the conductive particles (a), the barium sulfate particles (b) and the flexible resin (c).

7. A method for producing the garment comprising a wiring comprising a stretchable conductor composition according to claim 5, the method comprising:
   printing an electrical wiring on an intermediate medium by using a paste for forming a stretchable conductor; and thereafter; transferring the electrical wiring to a fabric,
   said paste comprising at least
   conductive particles (a),
   barium sulfate particles (b),
   a flexible resin (c) having a tensile elastic modulus of 1 MPa or more and 1000 MPa or less, and
   a solvent (d),
   wherein the barium sulfate particles (b) are contained in an amount of 2 to 30% by mass relative to the total amount of the conductive particles (a) and the barium sulfate particles (b), and the flexible resin (c) is contained in an amount of 7 to 35% by mass relative to the total amount of the conductive particles (a), the barium sulfate particles (b) and the flexible resin (c).

8. A garment comprising an electrical wiring comprising the stretchable conductor composition according to claim 1, wherein the electrical wiring comprises a layer formed of a stretchable conductor containing carbon as a conductive filler on a surface of the electrical wiring.

9. A garment comprising an electrical wiring comprising the stretchable conductor composition according to claim 1, wherein the electrical wiring comprises an insulating coating layer on a surface of the electrical wiring.

10. A garment comprising an electrical wiring comprising the stretchable conductor composition according to claim 1, wherein the electrical wiring comprises an insulating layer on a surface of the electrical wiring, the surface being in contact with a fabric constituting the garment.

11. A method for producing a garment comprising an electrical wiring, the method comprising:
    laminating a sheet formed of the stretchable conductor composition according to claim 1 on a fabric.

12. A paste for forming a stretchable conductor comprising at least
    conductive particles (a),
    barium sulfate particles (b),
    a flexible resin (c) having a tensile elastic modulus of 1 MPa or more and 1000 MPa or less, and
    a solvent (d),
    wherein the barium sulfate particles (b) are contained in an amount of 2 to 30% by mass relative to the total amount of the conductive particles (a) and the barium sulfate particles (b), and the flexible resin (c) is contained in an amount of 7 to 35% by mass relative to the total amount of the conductive particles (a), the barium sulfate particles (b) and the flexible resin (c).

13. The paste for forming a stretchable conductor according to claim 12,
    wherein the average particle diameter of the conductive particles as measured by a dynamic light scattering method is larger than the average particle diameter of the barium sulfate particles as measured by a dynamic light scattering method.

14. The paste for forming a stretchable conductor according to claim 12,
    wherein the barium sulfate particles are subjected to a surface treatment with a hydroxide and/or oxide of one or both of Al and Si.

15. The paste for forming a stretchable conductor according to claim 12,
    wherein the conductive particles comprise silver particles having an average particle diameter, as measured by a dynamic light scattering method, of 0.5 to 20 μm.

* * * * *